United States Patent
Marquais-Bienewald et al.

(10) Patent No.: US 7,722,893 B2
(45) Date of Patent: May 25, 2010

(54) USE OF SUBSTITUTE 2,4-BIS (ALKYLAMINO) PYRIMIDINES OR QUINZOLINES AS ANTIMICROBIALS

(75) Inventors: Sophie Marquais-Bienewald, Hegenheim (FR); Werner Hölzl, Eschentzwiller (FR); Andrea Preuss, Basel (CH); Andreas Mehlin, Rheinfelden (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 460 days.

(21) Appl. No.: 10/565,545

(22) PCT Filed: Jul. 16, 2004

(86) PCT No.: PCT/EP2004/051516

§ 371 (c)(1), (2), (4) Date: Jan. 23, 2006

(87) PCT Pub. No.: WO2005/011758

PCT Pub. Date: Feb. 10, 2005

(65) Prior Publication Data

US 2006/0188453 A1 Aug. 24, 2006

(30) Foreign Application Priority Data

Jul. 25, 2003 (EP) .................. 03102296

(51) Int. Cl.
*A01N 25/00* (2006.01)
*C07D 265/30* (2006.01)
*C07D 239/22* (2006.01)

(52) U.S. Cl. .................. 424/405; 544/122; 544/297

(58) Field of Classification Search .................. 424/405; 544/122, 297
See application file for complete search history.

(56) References Cited

U.S. PATENT DOCUMENTS

| | | | |
|---|---|---|---|
| 2,674,598 A | 4/1954 | Kyrides et al. | 260/256.4 |
| 4,116,674 A * | 9/1978 | Sunley et al. | 504/225 |
| 5,550,240 A * | 8/1996 | Mahó et al. | 544/295 |

FOREIGN PATENT DOCUMENTS

| | | |
|---|---|---|
| DE | 2403165 | 7/1975 |
| DE | 37 17 480 | 12/1988 |
| GB | 935381 | 8/1963 |
| GB | 1488093 | 10/1977 |

OTHER PUBLICATIONS

Derwent Abst. No. 88-347039/49 of DE 37 17 480.
D. Ghosh; J. Indian Chem. Soc., vol. LVIII, May 1981, pp. 512-513.
K. Ghoneim et al., J. Indian Chem. Soc. vol. LXIII, Oct. 1986, pp. 914-917.
T. Brzozowski et al., Dissert. Pharmacol., vol. 22,No. 2, 1970 pp. 117-125.
R. Gottasova et al., Folia Microbiol. vol. 43 (6), pp. 679-682 (1998).
N. Harris et al., Journal of Medicinal Chemistry, vol. 33, No. 1 (1990) pp. 435-444.
E. Coats et al., Eur. J. Med. Chem.—Chimica Therapeutica, May-June, vol. 14, No. 3, (1979) pp. 261-270.

* cited by examiner

*Primary Examiner*—Kamal A Saeed
*Assistant Examiner*—Samantha L Shterengarts
(74) *Attorney, Agent, or Firm*—Joseph C. Suhadolnik

(57) ABSTRACT

The use of 2,4—bis(alkylamino)pyrimidines of formula (1) $R_1$ is $C_1$-$C_{12}$alkyl or $C_6$-$C_{10}$aryl; $R_2$ is hydrogen or $C_1$-$C_{12}$alkyl; or $R_1$ and $R_2$ together form a radical of formula (1a) R' and R" are each independently of the other hydrogen, $C_1$-$C_6$alkyl or $C_1$-$C_6$alkoxy, $R_3$ and $R_5$ are each independently of the other hydrogen or $C_1$-$C_8$alkyl; $R_4$ is $C_1$-$C_{20}$alkyl, unsubstituted phenyl, $C_6$-$C_{10}$aryl, $C_6$-$C_{10}$aryl-$C_1$-$C_6$alkyl, hydroxy-$C_1$-$C_6$alkyl, di-$C_1$-$C_6$alkylamino-$C_1$-$C_6$alkyl, mono-$C_1$-$C_6$alkylamino-$C_1$-$C_6$alkyl, —$(CH_2)_2$—$(O$—$(CH_2)_2)_{1-4}$—OH or —$(CH_2)_2$—$(O$—$(CH_2)_2)_{1-4}$—$NH_2$; $R_6$ is $C_1$-$C_{20}$alkyl, $C_6$-$C_{10}$aryl, $C_6$-$C_{10}$aryl-$C_1$-$C_6$alkyl, hydroxy-$C_1$-$C_6$alkyl, di-$C_1$C_6$alkylamino-$C_1$-$C_6$alkyl, mono-$C_1$-$C_6$alkylamino-$C_1$-$C_6$alkyl, —$(CH_2)_2$—$(O$—$(CH_2)_2)_{1-4}$—OH or —$(CH_2)_2$—$(O$—$(CH_2)_2)_{1-4}$—$NH_2$; or $R_3$ and $R_4$ and/or $R_5$ and $R_6$, together form a pyrrolidine, piperidine, hexamethyleneimine or morpholine ring; in the antimicrobial treatment of surfaces.

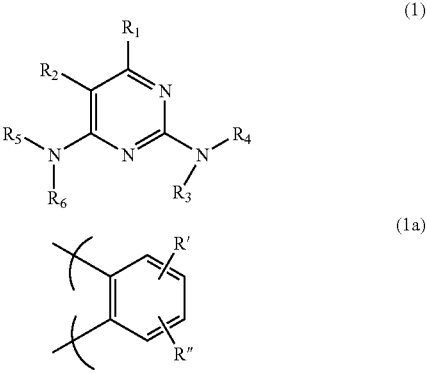

11 Claims, No Drawings

USE OF SUBSTITUTE 2,4-BIS (ALKYLAMINO) PYRIMIDINES OR QUINZOLINES AS ANTIMICROBIALS

The present invention relates to the use of substituted 2,4-bis(alkylamino)pyrimidines in the antimicrobial treatment of surfaces and to the preparation of such compounds.

The present invention relates to the use of 2,4-bis(alkylamino)pyrimidines of formula

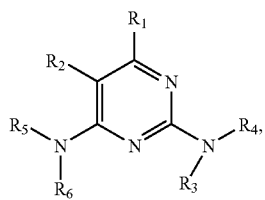

wherein
$R_1$ is $C_1$-$C_{12}$alkyl or $C_6$-$C_{10}$aryl;
$R_2$ is hydrogen or $C_1$-$C_{12}$alkyl; or $R_1$ and $R_2$ together form a radical of formula

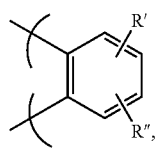

wherein
R' and R''' are each independently of the other hydrogen, $C_1$-$C_6$alkyl or $C_1$-$C_6$alkoxy;
$R_3$ and $R_5$ are each independently of the other hydrogen or $C_1$-$C_8$alkyl;
$R_4$ is $C_1$-$C_{20}$alkyl, unsubstituted phenyl, $C_6$-$C_{10}$aryl, preferred $C_7$-$C_{10}$aryl; $C_6$-$C_{10}$aryl-$C_1$-$C_8$alkyl, hydroxy-$C_1$-$C_6$alkyl, di-$C_1$-$C_6$alkylamino-$C_1$-$C_6$alkyl, mono-$C_1$-$C_6$alkylamino-$C_1$-$C_8$alkyl, —$(CH_2)_2$(O—$(CH_2)_2)_{1-4}$—OH or —$(CH_2)_2$—(O—$(CH_2)_2)_{1-4}$—$NH_2$;
$R_6$ is $C_1$-$C_{20}$alkyl, $C_8$-$C_{10}$aryl, $C_6$-$C_{10}$aryl-$C_1$-$C_8$alkyl, hydroxy-$C_1$-$C$alkyl, di-$C_1$-$C_8$alkylamino-$C_1$-$C$alkyl, mono-$C_1$-$C_6$alkylamino-$C_1$-$C_6$alkyl, —$(CH_2)_2$—(O—$(CH_2)_2)_{1-4}$—OH or —$(CH_2)_2$—(O—$(CH_2)_2)_{1-4}$—$NH_2$; or
$R_3$ and $R_4$ and/or $R_5$ and $R_6$ together form a pyrrolidine, piperidine, hexamethyleneimine or morpholine ring;

in the antimicrobial treatment of surfaces.

$C_1$-$C_{20}$Alkyl is straight-chain or branched alkyl, e.g. methyl, ethyl, n-propyl, isopropyl, n-butyl, sec-butyl, tert-butyl, amyl, isoamyl or tert-amyl, hexyl, isohexyl, heptyl, octyl, isooctyl, nonyl, decyl, undecyl, dodecyl, tetradecyl, pentadecyl, hexadecyl, heptadecyl, octadecyl or eicosyl.

$C_1$-$C_{12}$Alkyl is straight-chain or branched alkyl, e.g. methyl, ethyl, n-propyl, isopropyl, n-butyl, sec-butyl, tert-butyl, amyl, isoamyl or tert-amyl, hexyl, isohexyl, heptyl, octyl, isooctyl, nonyl, decyl, undecyl or dodecyl.

$C_1$-$C_8$Alkyl is straight-chain or branched alkyl, e.g. methyl, ethyl, n-propyl, isopropyl, n-butyl, sec-butyl, tert-butyl, amyl, isoamyl or tert-amyl, isohexyl, hexyl, heptyl, octyl or isooctyl.

$C_1$-$C_4$Alkyl is straight-chain or branched alkyl, e.g. methyl, ethyl, n-propyl, isopropyl, n-butyl, sec-butyl or tert-butyl.
$C_1$-$C_8$Alkyl is straight-chain or branched alkyl, e.g. n-propyl, isopropyl, n-butyl, sec-butyl, tert-butyl, amyl, isoamyl or tert-amyl, isohexyl, hexyl, heptyl, octyl or isooctyl, especially hexyl.
$C_1$-$C_6$Alkyl is straight-chain or branched alkyl, e.g. methyl, ethyl, n-propyl, isopropyl, n-butyl, sec-butyl, tert-butyl, amyl, isoamyl or tert-amyl, hexyl or isohexyl.
$C_1$-$C_6$Alkoxy is a straight-chain or branched radical, e.g. methoxy, ethoxy, propoxy, butoxy, pentyloxy or hexyloxy.
$C_6$-$C_{10}$Aryl denotes naphthyl and especially phenyl. $C_6$-$C_{10}$Aryl radicals may be unsubstituted or may carry one or more, for example one, two, three or four, identical or different substituents, which may be in any desired position(s). Examples of such substituents are $C_1$-$C_4$alkyl, halogen, hydroxy, $C_1$-$C_4$alkoxy, trifluoromethyl, cyano, hydroxycarbonyl, $C_1$-$C_4$-alkoxycarbonyl, aminocarbonyl, amino, $C_1$-$C_4$alkylamino, di-$C_1$-$C_4$alkylamino and $C_1$-$C_4$-alkylcarbonylamino.

Special preference is given to compounds of formula (1) wherein
$R_1$ is $C_1$-$C_8$alkyl or phenyl;

or to compounds of formula (1) wherein
$R_2$ is hydrogen or $C_3$-$C_8$alkyl;

or to compounds of formula (1) wherein
$R_3$ and $R_5$ are each independently of the other hydrogen or $C_1$-$C_8$alkyl;

or to compounds of formula (1) wherein
$R_4$ is $C_1$-$C_{12}$alkyl, unsubstituted phenyl, $C_6$-$C_{10}$aryl-$C_1$-$C_6$alkyl, hydroxy-$C_2$-$C_6$alkyl, di-$C_1$-$C_4$-alkylamino-$C_1$-$C_4$alkyl, mono-$C_1$-$C_4$alkylamino-$C_1$-$C_4$alkyl, —$(CH_2)_2$—(O—$(CH_2)_2)_{1,2}$—OH or —$(CH_2)_2$—(O—$(CH_2)_2)_{1,2}$—$NH_2$; and
$R_6$ is $C_1$-$C_{12}$alkyl, $C_6$-$C_{10}$aryl, $C_6$-$C_{10}$aryl-$C_1$-$C_6$alkyl, hydroxy-$C_2$-$C_6$alkyl, di-$C_1$-$C_4$alkylamino-$C_1$-$C_4$alkyl, mono-$C_1$-$C_4$alkylamino-$C_1$-$C_4$alkyl, —$(CH_2)_2$—(O—$(CH_2)_2)_{1,2}$—OH or —$(CH_2)_2$—(O—$(CH_2)_2)_{1,2}$—$NH_2$;

or to compounds of formula (1) wherein
$R_3$ and $R_4$ and/or $R_6$ and $R_6$ together form a pyrrolidine, piperidine, hexamethyleneimine or morpholine ring.

Preference is given to the use according to the invention of compounds of formula

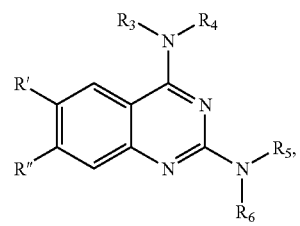

wherein
R' is hydrogen, $C_1$-$C_3$alkyl or $C_1$-$C_3$alkoxy;
R'' is $C_1$-$C_3$alkyl or $C_1$-$C_3$alkoxy;
$R_3$ and $R_5$ are each independently of the other hydrogen or $C_1$-$C_8$alkyl; and
$R_4$ and $R_6$ are each independently of the other $C_1$-$C_{12}$alkyl, phenyl-$C_1$-$C_3$alkyl, hydroxy-$C_1$-$C_6$-alkyl or di-$C_1$-

$C_6$alkylamino-$C_1$-$C_6$alkyl, mono-$C_1$-$C_6$alkylamino-$C_1$-$C_6$alkyl, —(CH$_2$)$_2$—(O—(CH$_2$)$_2$)$_{1-4}$—OH or —(CH$_2$)$_2$—(O—(CH$_2$)$_2$)$_{1-4}$—NH$_2$; or $R_3$ and $R_4$ and/or $R_5$ and $R_6$ together form a pyrrolidine, piperidine, hexamethyleneimine or morpholine ring.

Special preference is given to the use of compounds of formula (1) wherein $R_1$ is $C_1$-$C_8$ or phenyl;

$R_2$ is hydrogen or hexyl; or $R_1$ and $R_2$ together form a radical of formula (1a) wherein R' is hydrogen, $C_1$-$C_3$alkyl or $C_1$-$C_3$alkoxy, and R" is $C_1$-$C_3$alkyl or $C_1$-$C_3$alkoxy;

$R_3$ and $R_5$ are each independently of the other hydrogen or $C_1$-$C_8$alkyl;

$R_4$ is $C_1$-$C_{12}$alkyl, unsubstituted phenyl, $C_6$-$C_{10}$aryl-$C_1$-$C_6$alkyl, hydroxy-$C_2$-$C_6$alkyl, di-$C_1$-$C_4$-alkylamino-$C_1$-$C_4$alkyl, mono-$C_1$-$C_4$alkylamino-$C_1$-$C_4$alkyl, —(CH$_2$)$_2$—(O—(CH$_2$)$_2$)$_{1,2}$—OH or —(CH$_2$)$_2$—(O—(CH$_2$)$_2$)$_{1,2}$—NH$_2$; and $R_6$ is $C_1$-$C_{12}$alkyl, $C_6$-$C_{10}$aryl, $C_6$-$C_{10}$aryl-$C_1$-$C_6$alkyl, hydroxy-$C_2$$C_6$alkyl, di-$C_1$-$C_4$alkyl-amino-$C_1$-$C_4$alkyl, mono-$C_1$-$C_4$alkylamino-$C_1$-$C_4$alkyl, —(CH$_2$)$_2$—(O—(CH$_2$)$_2$)$_{1,2}$—OH or —(CH$_2$)$_2$—(O—CH$_2$)$_2$)$_{1,2}$—NH$_2$; or $R_3$ and $R_4$ together, and $R_5$ and $R_6$ together, form a pyrrolidine, piperidine, hexamethyleneimine or morpholine ring.

There are used especially compounds of formula (1) wherein $R_3$ and $R_5$, and $R_4$ and $R_6$, have the same meanings.

Especially preferred compounds are those of the following formulae

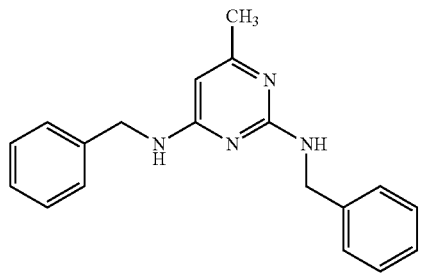

and

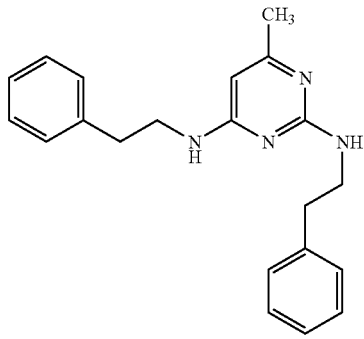

and

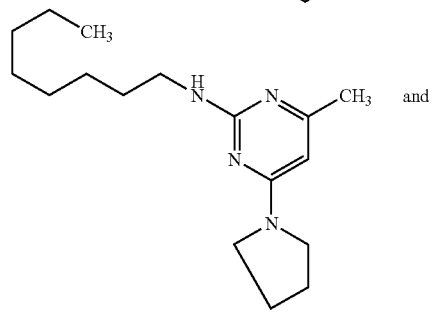

and

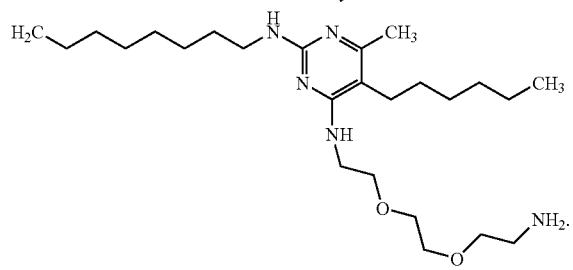

Examples of compounds used according to the invention are listed in Table 1:

TABLE 1

| Compound of formula | Structure | Mass | Purity GC (%) | Purity LC (%) |
|---|---|---|---|---|
| PY1 | 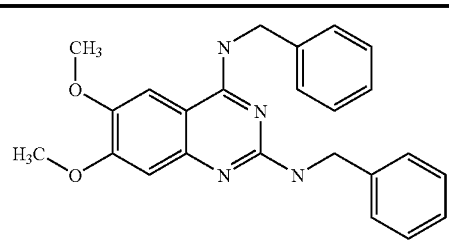 | 400 | 25 (GC) | |
| PY2 | 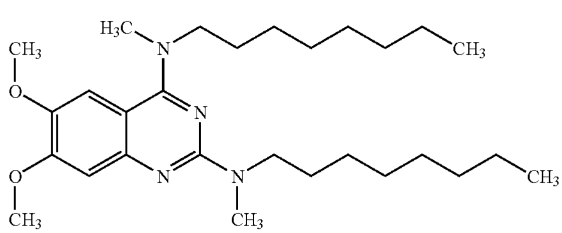 | 473 | 80 (GC) | |

TABLE 1-continued

| Compound of formula | Structure | Mass | Purity GC (%) | Purity LC (%) |
|---|---|---|---|---|
| PY3 | 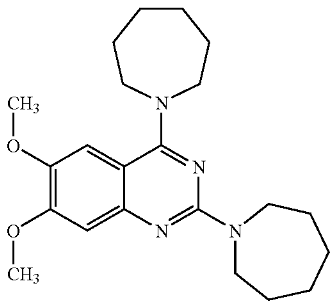 | 385 | 78 (GC) | |
| PY4 | 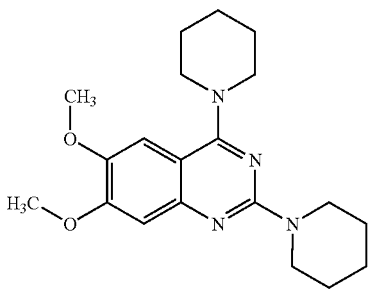 | 356 | 100 (GC) | |
| PY5 | 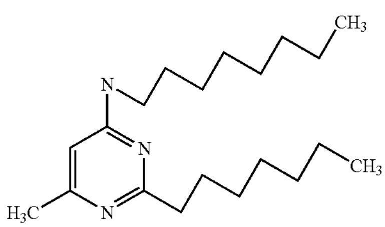 | 349 | 98 (GC) | |
| PY6 | 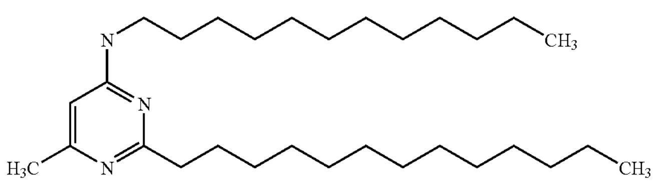 | 461 | 35 (GC) | |
| PY7 | 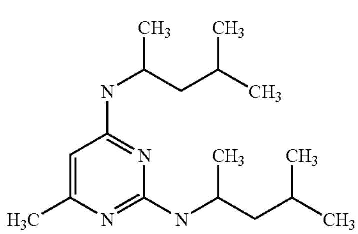 | 292 | 100 (GC) | |
| PY8 | 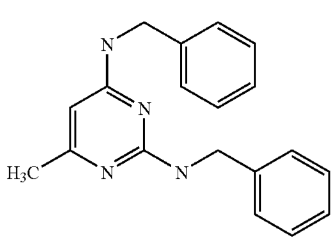 | 304 | 100 (GC) | |

TABLE 1-continued

| Compound of formula | Structure | Mass | Purity GC (%) | Purity LC (%) |
|---|---|---|---|---|
| PY9 | 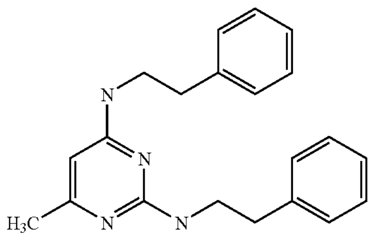 | 332 | 100 (GC) | |
| PY10 | 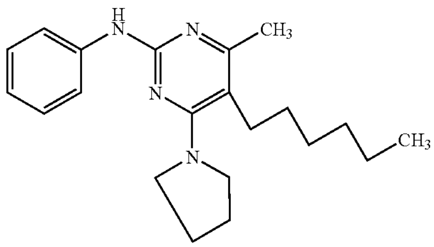 | 339 | | 97 (LC) |
| PY11 | 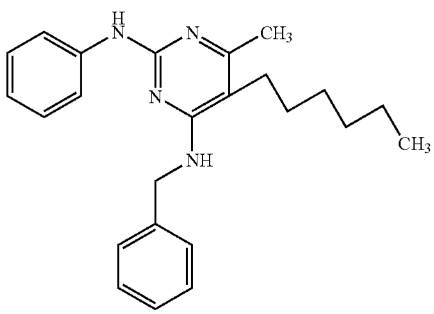 | 375 | | 50 (LC) |
| Py12 | 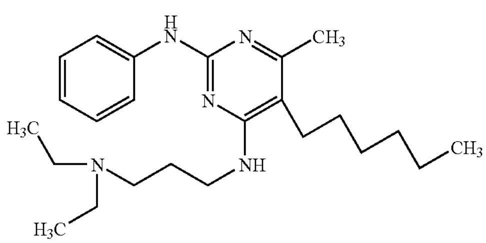 | 398 | | 70 (LC) |
| PY13 | 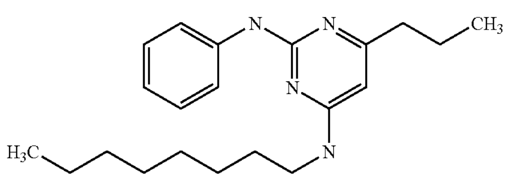 | 341 | | 94 (LC) |
| PY14 | 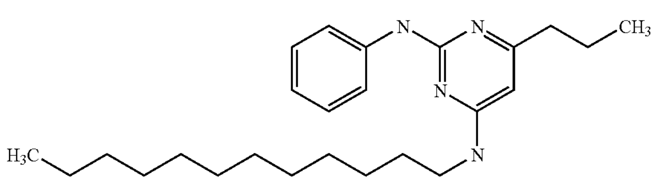 | 397 | | 90 (LC) |

TABLE 1-continued

| Compound of formula | Structure | Mass | Purity GC (%) | Purity LC (%) |
|---|---|---|---|---|
| PY15 | 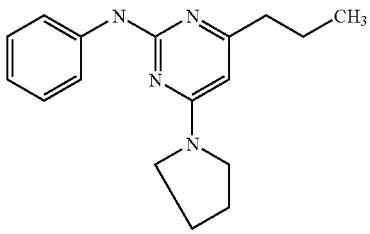 | 282 | | 96 (LC) |
| PY16 | 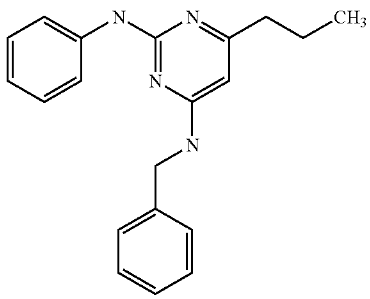 | 318 | | 82 (LC) |
| PY17 | 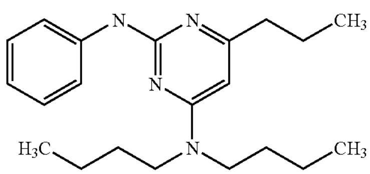 | 341 | | 60 (LC) |
| PY18 | 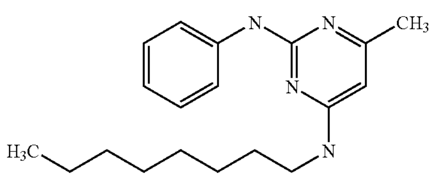 | 312 | | 98 (LC) |
| PY19 | 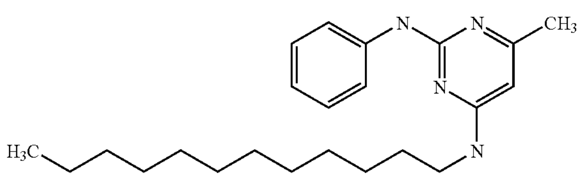 | 369 | | 84 (LC) |
| PY20 | 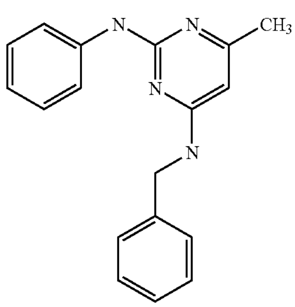 | 290 | | 97 (LC) |
| PY21 | 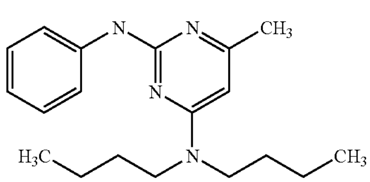 | 312 | | 85 (LC) |

TABLE 1-continued

| Compound of formula | Structure | Mass | Purity GC (%) | Purity LC (%) |
|---|---|---|---|---|
| PY22 | 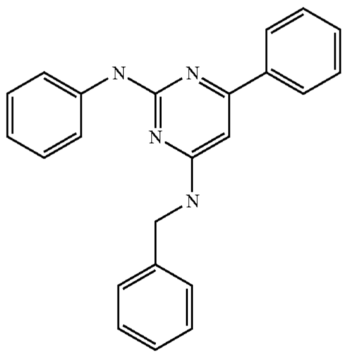 | 352 | | 89 (LC) |
| PY23 | 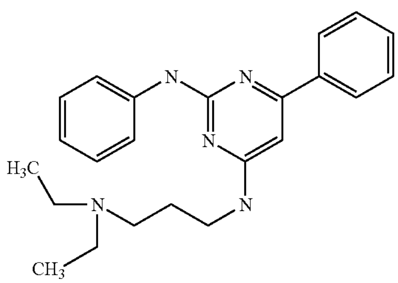 | 376 | | 96 (LC) |
| PY24 | 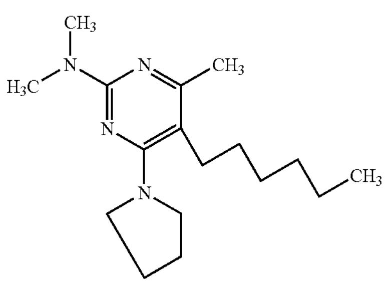 | 290 | | 99 (LC) |
| PY25 | 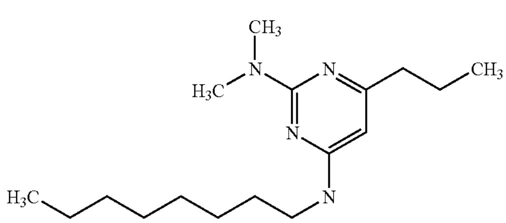 | 292 | | 92 (LC) |
| PY26 | 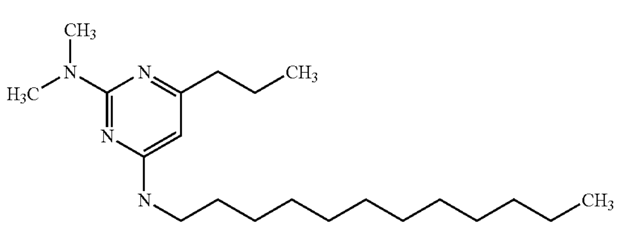 | 349 | | 88 (LC) |

TABLE 1-continued

| Compound of formula | Structure | Mass | Purity GC (%) | Purity LC (%) |
|---|---|---|---|---|
| PY27 | 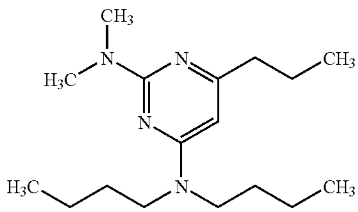 | 292 | | 93 (LC) |
| PY28 | 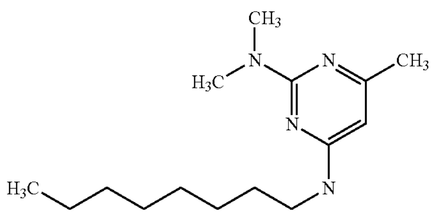 | 264 | | 77 (LC) |
| PY29 | 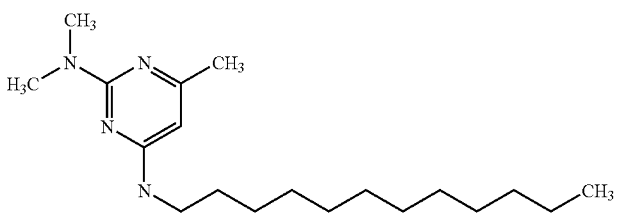 | 321 | | 93 (LC) |
| PY30 | 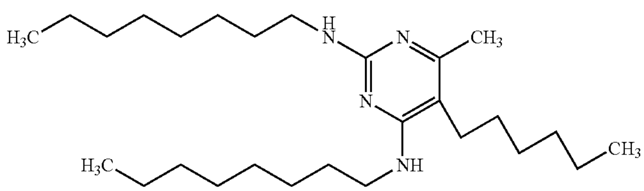 | 433 | | 68 |
| PY31 | 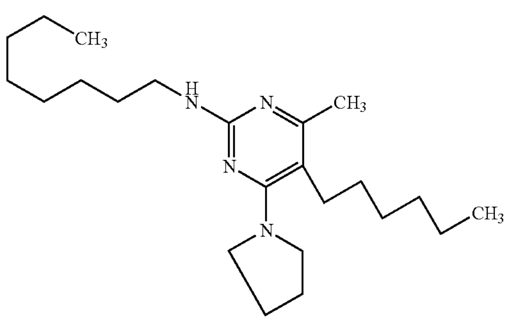 | 375 | | 97 |
| PY32 | 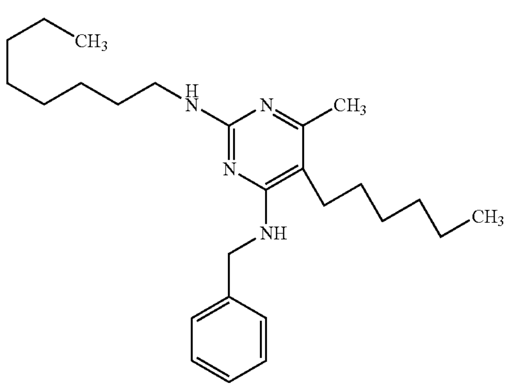 | 411 | | 26 |

TABLE 1-continued

| Compound of formula | Structure | Mass | Purity GC (%) | Purity LC (%) |
|---|---|---|---|---|
| PY33 | 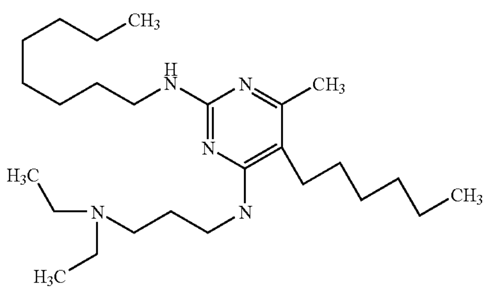 | 434 | | 58 |
| PY34 | 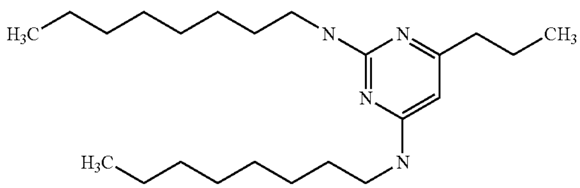 | 377 | | 84 |
| PY35 | 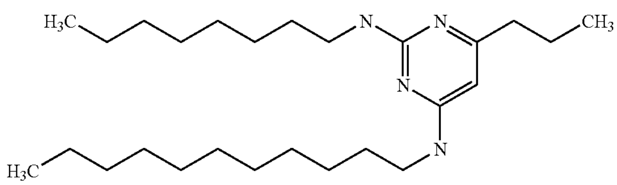 | 433 | | 77 |
| PY36 | 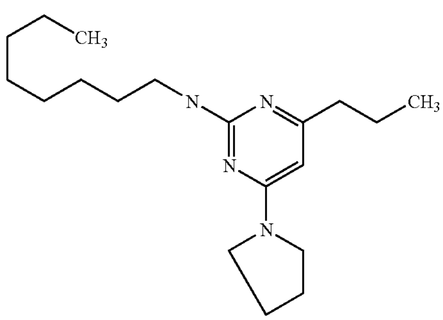 | 319 | | 99 |
| PY37 | 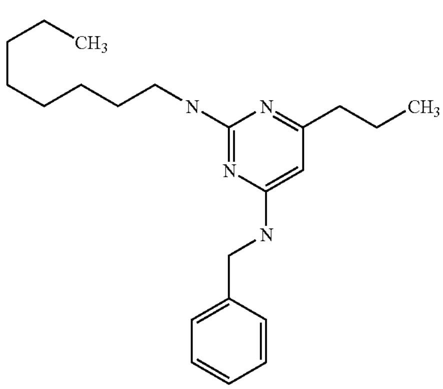 | 355 | | 77 |

TABLE 1-continued
| Compound of formula | Structure | Mass | Purity GC (%) | Purity LC (%) |
|---|---|---|---|---|
| PY38 | 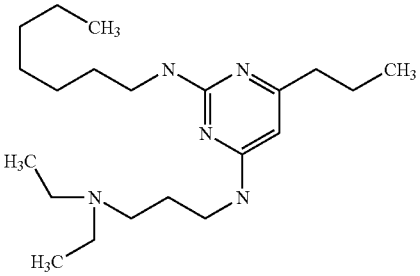 | 378 | | 73 |
| PY39 | 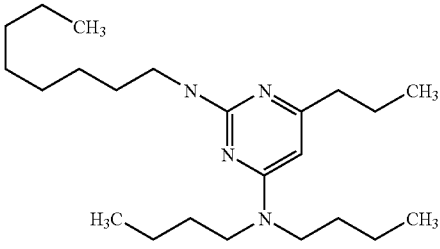 | 377 | | 65 |
| PY40 | 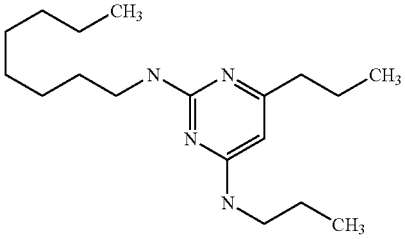 | 306 | | 32 |
| PY41 | 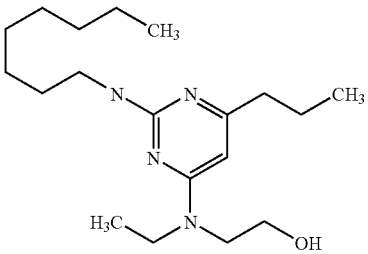 | 337 | | 91 |
| PY42 | 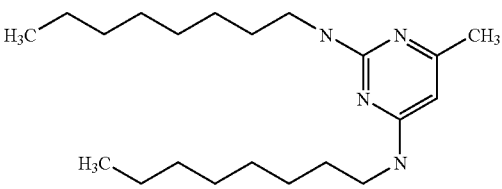 | 349 | | 90 |
| PY43 | 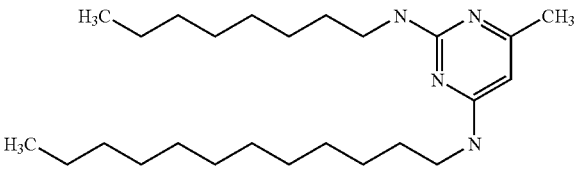 | 405 | | 83 |

TABLE 1-continued

| Compound of formula | Structure | Mass | Purity GC (%) | Purity LC (%) |
|---|---|---|---|---|
| PY44 | 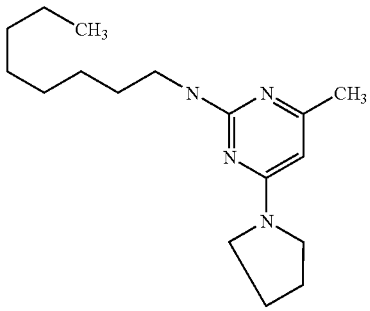 | 290 | | 99 |
| PY45 | 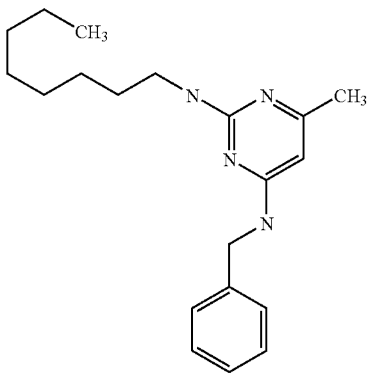 | 326 | | 51 |
| PY46 | 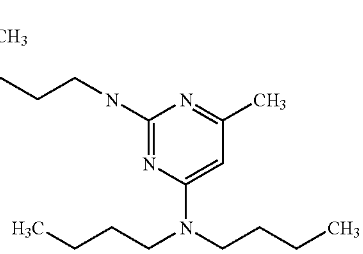 | 349 | | 72 |
| PY47 | 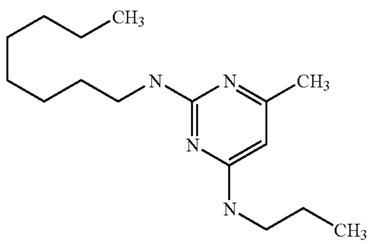 | 278 | | 55 |
| PY48 | 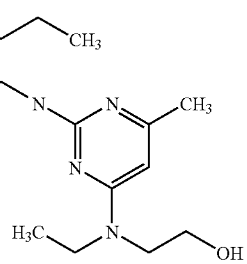 | 308 | | 90 |

TABLE 1-continued
| Compound of formula | Structure | Mass | Purity GC (%) | Purity LC (%) |
|---|---|---|---|---|
| PY49 | 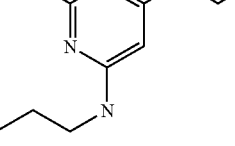 | 411 | | 87 |
| PY50 | 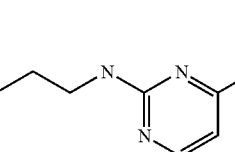 | 467 | | 90 |
| PY51 | 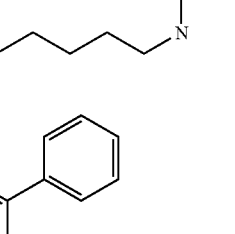 | 353 | | 97 |
| PY52 | 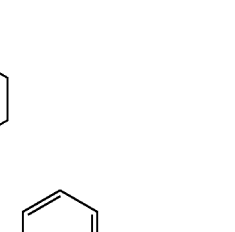 | 412 | | 94 |
| PY53 | 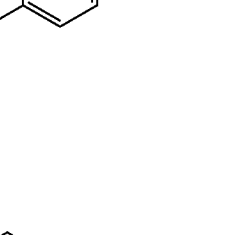 | 371 | | 57 |
| PY54 | 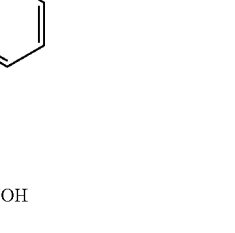 | 335 | | 85 |

TABLE 1-continued

| Compound of formula | Structure | Mass | Purity GC (%) | Purity LC (%) |
|---|---|---|---|---|
| PY55 | 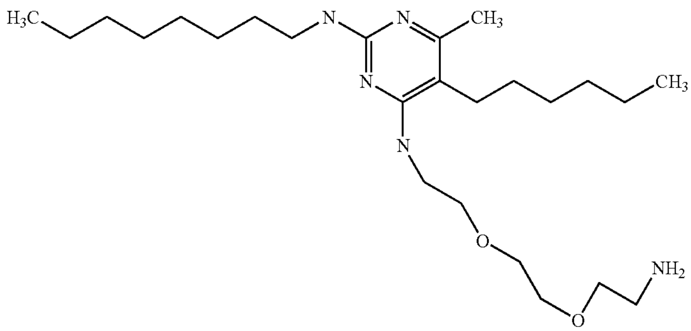 | 452 | | 49 |
| PY56 | 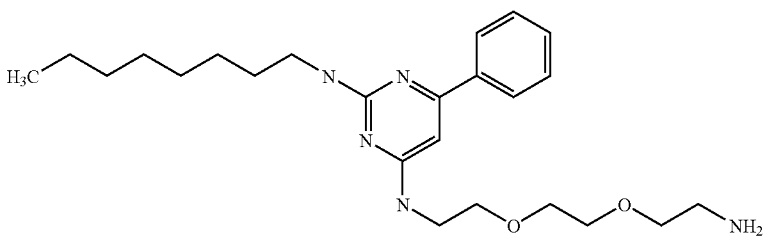 | 430 | | 40 |
| PY57 | 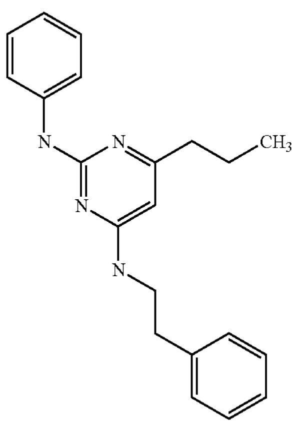 | 332 | | 70 |
| PY58 | 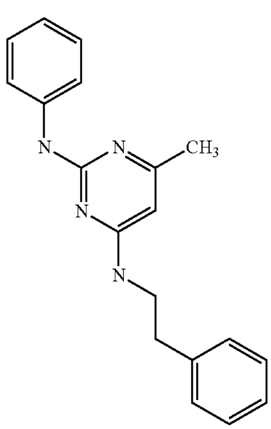 | 304 | | 78 |

TABLE 1-continued

| Compound of formula | Structure | Mass | Purity GC (%) | Purity LC (%) |
|---|---|---|---|---|
| PY59 | 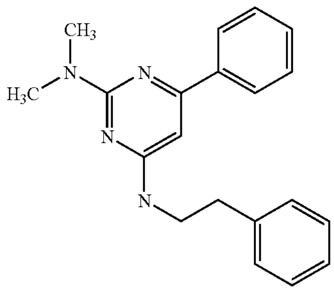 | 318 | | 65 |
| PY60 | 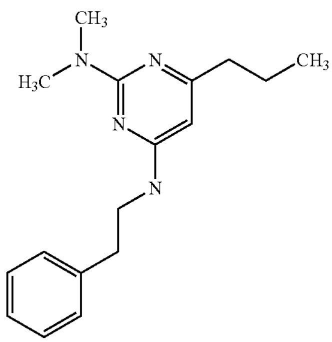 | 284 | | 48 |
| PY61 | 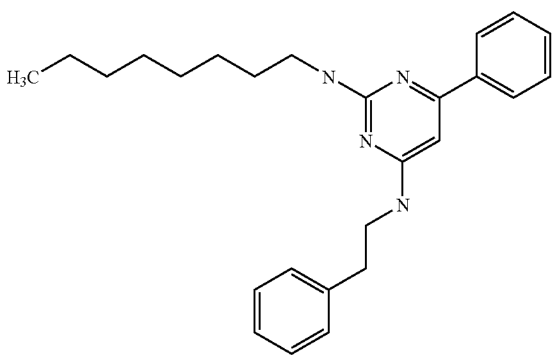 | 403 | | 74 |
| PY62 | 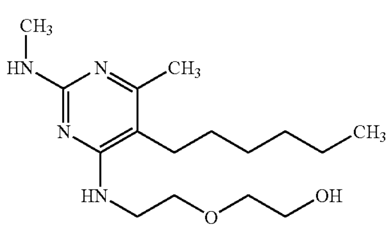 | 310 | | 78 |
| PY63 | 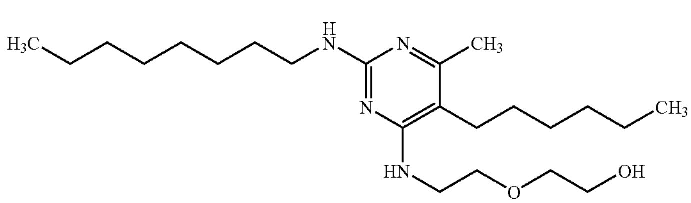 | 409 | | 61 |

TABLE 1-continued

| Compound of formula | Structure | Mass | Purity GC (%) | Purity LC (%) |
|---|---|---|---|---|
| PY64 | 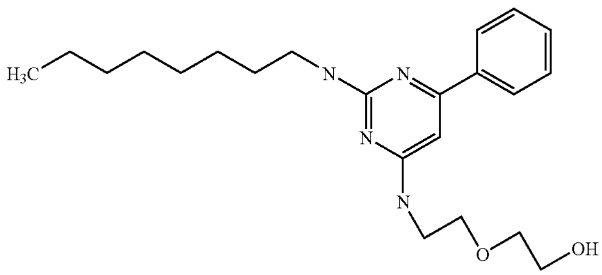 | 387 | | 56 |
| PY65 | 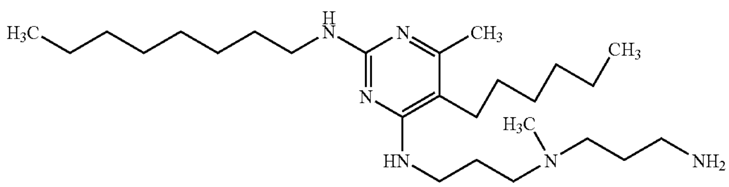 | 449 | | 28 |
| PY66 | 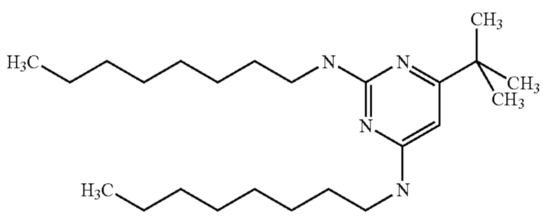 | 391 | | 93 |
| PY67 | 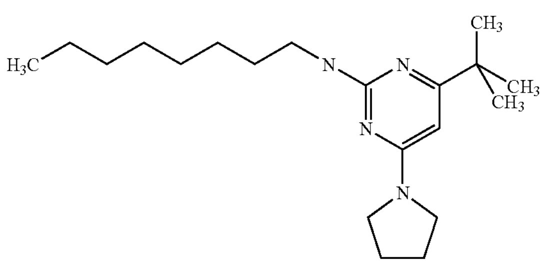 | 333 | | 90 |
| PY68 | 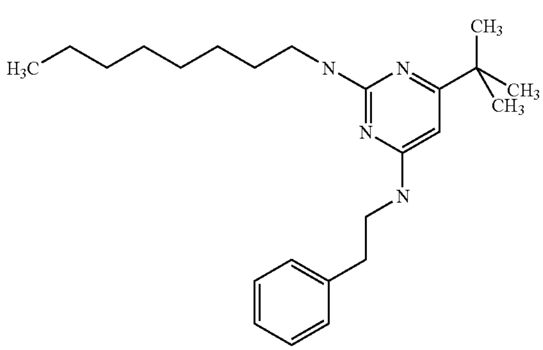 | 383 | | 90 |

TABLE 1-continued

| Compound of formula | Structure | Mass | Purity GC (%) | Purity LC (%) |
|---|---|---|---|---|
| PY69 | 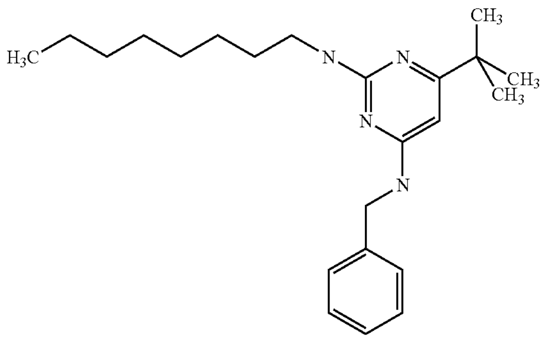 | 369 | | 75 |
| PY70 | 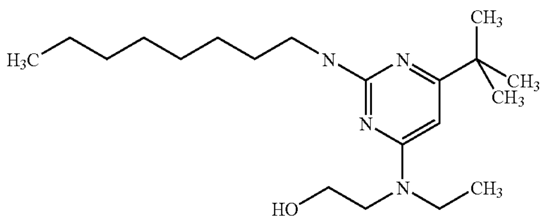 | 351 | | 94 |
| PY71 | 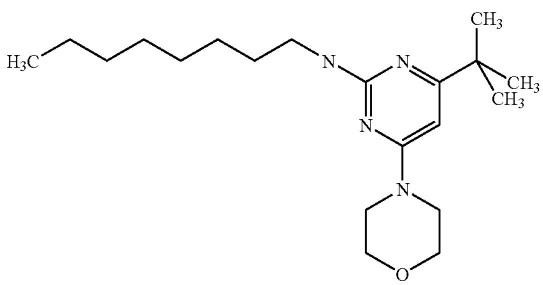 | 349 | | 91 |
| PY72 | 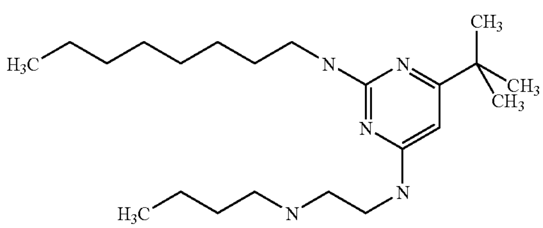 | 378 | | 87 |
| PY73 | 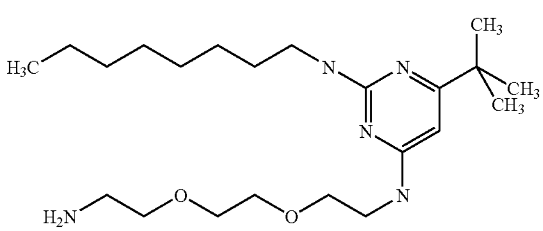 | 410 | | 48 |
| PY74 | 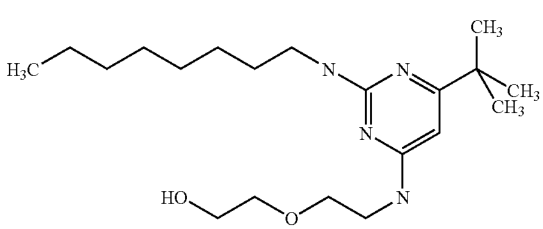 | 367 | | 92 |

The compounds used according to the invention are prepared according to methods known per se. The substituted 2,4-bis(alkylamino)pyrimidines are obtained by reacting the corresponding dichloropyrimidine compound (formula (1b)) with a primary or secondary amine-depending upon the meanings of the radicals $R_3$ and $R_5$— in a suitable solvent, e.g. DMF, di-oxane, toluene, xylene, ethanol or butanol, and an auxiliary base, e.g. triethylamine, DIEA, sodium carbonate, potassium carbonate, etc., or using an excess of the amine compound, for a period of from 1 to 24 hours at 40-150° C. The reaction takes place according to the following Scheme (I):

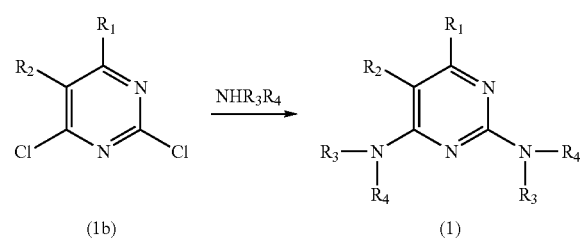

(1b)          (1)

or the compounds used according to the invention are prepared by condensing a guanidine compound with a suitable β-keto ester using an auxiliary base, e.g. sodium carbonate, potassium carbonate, sodium ethanolate, sodium methanolate or potassium tert-butanolate, in a suitable solvent, e.g. methanol, ethanol, butanol, tert-butanol, tetrahydrofuran, dimethylformamide, acetonitrile, toluene or xylene, for a period of from 1 hour to 24 hours at a temperature of from 40 to 150° C. The resulting 2-alkylamino-4-hydroxy-pyrimidine is then converted into the corresponding 2-alkylamino-4-chloro-pyrimidine compound according to customary methods by means of phosphorus oxychloride.

The substituted 2,4-alkylamino-pyrimidines are obtained by reacting the 2-alkylamino-4-chloro-pyrimidine compound with a primary or secondary amine ($R_4R_5NH$) in a suitable solvent, e.g. methanol, ethanol, butanol, tetrahydrofuran, dimethylformamide, dioxane, toluene or xylene, and an auxiliary base, e.g. triethylamine, DIEA, sodium carbonate, potassium carbonate or an excess of amine, for a period of from 1 to 24 hours at a temperature of from 40 to 150° C. The reaction takes place according to the following Scheme (II):

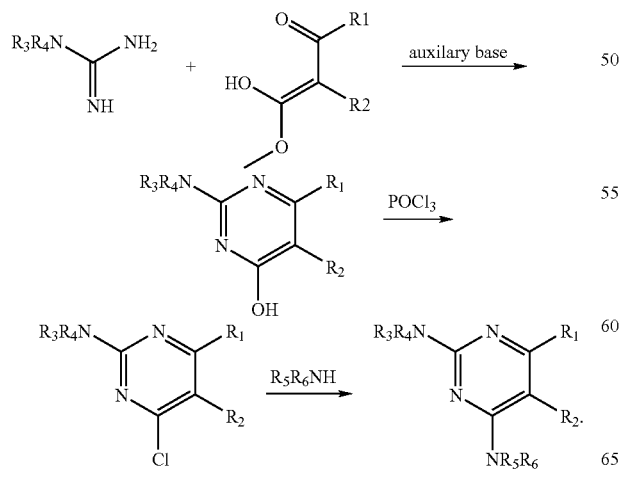

The 2,4-bis(alkylamino)pyrimidines used according to the invention exhibit a pronounced antimicrobial action, especially against pathogenic gram-positive and gram-negative bacteria and against bacteria of skin flora, and also against yeasts and moulds. They are therefore suitable especially in the disinfection, deodorisation and the general and antimicrobial treatment of the skin and mucosa and also of integumentary appendages (hair), more especially in the disinfection of the hands and of wounds.

They are therefore suitable as antimicrobial active ingredients and preservatives in personal care preparations, for example shampoos, bath additives, hair-care products, liquid and solid soaps (based on synthetic surfactants and salts of saturated and/or unsaturated fatty adds), lotions and creams, deodorants, other aqueous or alcoholic solutions, e.g. cleansing solutions for the skin, moist cleansing cloths, oils or powders.

The invention therefore relates also to a personal care preparation comprising at least one compound of formula (1) as well as cosmetically tolerable carriers or adjuvants. The personal care preparation according to the invention contains from 0.01 to 15% by weight, preferably from 0.1 to 10% by weight, based on the total weight of the composition, of a compound of formula (1) and cosmetically tolerable adjuvants.

Depending upon the form of the personal care preparation, it will comprise, in addition to the 2,4-bis(alkylamino)pyrimidine of formula (1), further constituents, for example sequestering agents, colourings, perfume oils, thickening or solidifying agents (consistency regulators), emollients, UV absorbers, skin-protective agents, antioxidants, additives that improve mechanical properties, such as dicarboxylic acids and/or Al, Zn, Ca and Mg salts of $C_{14}$-$C_{22}$ fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention may be used in a variety of fields. Especially the following preparations, for example, come into consideration:

skin-care preparations, e.g. skin-washing and cleansing preparations in the form of tablet-form or liquid soaps, synthetic detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-mare preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:
0.01 to 5% by weight of a compound of formula (1)
0.3 to 1% by weight titanium dioxide
1 to 10% by weight stearic acid
ad 100% soap base, e.g. the sodium salts of tallow fatty acid and coconut fatty acid or glycerol.

A shampoo has, for example, the following composition:
0.01 to 5% by weight of a compound of formula (1)
12.0% by weight sodium laureth-2-sulfate
4.0% by weight cocamidopropyl betaine
3.0% by weight NaCl and water ad 100%.

A deodorant has, for example, the following composition:
0.01 to 5% by weight of a compound of formula (1)
60% by weight ethanol
0.3% by weight perfume oil and water ad 100%.

The invention relates also to an oral composition containing from 0.01 to 15% by weight, based on the total weight of the composition, of a compound of formula (1) and orally tolerable adjuvants.

Example of an oral composition:
10% by weight sorbitol
10% by weight glycerol
15% by weight ethanol
15% by weight propylene glycol
0.5% by weight sodium lauryl sulfate
0.25% by weight sodium methyloocyl taurate
0.25% by weight polyoxypropylene/polyoxyethylene block copolymer
0.10% by weight peppermint flavouring
0.1 to 0.5% by weight of a compound of formula (1) and 48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The 2,4-bis(alkylamino)pyrimidines of formula (1) used according to the invention are also suitable for the treatment, especially preservation, of textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The 2,4-bis(alkylamino)pyrimidines according to the invention are also suitable for the treatment of plastics, especially for imparting antimicrobial properties to or preserving plastics, e.g. polyethylene, polypropylene, polyurethane, polyester, polyamide, polycarbonate, latex etc. Fields of use therefor are, for example, floor coverings, plastics coatings, plastics container and packaging materials; kitchen and bathroom utensils (e.g. brushes, shower curtains; sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with anti-microbial properties using the 2,4-bis(alkylamino)pyrimidines of formula (1) according to the invention.

It is also possible for nonwovens, e.g. nappies/diapers, sanitary towels, panty liners, and cloths for hygiene and household uses, to be provided with antimicrobial properties in accordance with the invention.

The 2,4-bis(alkylamino)pyrimidines of formula (1) are also used in washing and cleaning formulations, e.g. in liquid and powder washing agents or softeners.

The 2,4-bis(alkylamino)pyrimidines of formula (1) may especially also be used in household and all-purpose cleaners for cleaning and disinfecting hard surfaces.

A cleaning preparation has, for example, the following composition:
0.01 to 5% by weight of a compound of formula (1)
3.0% by weight octyl alcohol 4EO
1.3% by weight fatty alcohol $C_8$-$C_{10}$ polyglucoside
3.0% by weight isopropanol
ad 100% by weight water.

In addition to preserving cosmetic and household products, the preservation of technical products, the provision of technical products with antimicrobial properties and use as a biocide in technical processes are also possible, for example in paper treatment, especially in paper treatment liquors, in printing ink thickeners consisting of starch or of cellulose derivatives, in surface-coating compositions and in paints.

The 2,4-bis(alkylamino)pyrimidines of formula (1) are also suitable for the antimicrobial treatment of wood and for the antimicrobial treatment of leather, the antimicrobial preservation of leather and the provision of leather with antimicrobial properties.

The compounds according to the invention are also suitable for the protection of cosmetic products and household products from microbial spoilage.

In addition to their generally antimicrobial action, the 2,4-bis(alkylamino)pyrimidines of formula (1) according to the invention are moreover capable of penetrating biofilms on living and non-living surfaces, of preventing the adhesion of bacteria to surfaces and any further build-up of the biofilm, of detaching such biofilm and/or inhibiting the further growth of the biofilm-forming micro-ogranisms in the biological matrix, or of killing such micro-organisms.

Biofilms are understood, very generally, to be aggregations of living and dead micro-organisms, especially bacteria, that adhere to living and non-living surfaces, together with their metabolites in the form of extracellular polymeric substances (EPS matrix), e.g. polysaccharides. The activity of antimicrobial substances that normally exhibit a pronounced growth-inhibiting or lethal action with respect to planktonic cells may be greatly reduced with respect to microorganisms that are organised in biofilms, for example because of inadequate penetration of the active substance into the biological matrix.

In the present invention, this relates, very especially, to biofilms on human tooth surfaces and oral mucosa, which play a crucial role in the onset of degenerative diseases in the oral cavity, e.g. caries or periodontitis, as a result of the biofilm-forming micro-organisms or their metabolites.

The following Examples illustrate, but do not limit, the present invention.

IMPLEMENTATION EXAMPLES

Example 1

Preparation of N,N'-bis(2A-dioctylamino-6-methyliprimidine (PY5)

8.15 g of 2,4-dichloro-6-methyl-pyrimidine (50 mmol) are heated with 19.39 g of octylamine (150 mmol) and 20.73 g of potassium carbonate (150 mmol) in 20 ml of dioxane for 16 hours at 100° C. After cooling, the product is taken up in 300 ml of ethyl acetate and washed with 0.5 mol/liter of sodium hydroxide solution and saturated sodium chloride solution. The product is concentrated in vacuo and then octylamine is distilled off for 2 hours at 140° C. under a rotary slide valve vacuum. 12.95 g of N,N'-bis(2,4-dioctylamino)-6-methylpyrimidine (37.15 mmol, 74.3% of theory) are obtained. The end product is analysed by NMR, HPLC-MS, GC and HPLC.

GC: 98% area

M+1=349

NMR ($^1$H in DMSO): 0.85, t, 6H; 1.25, m, 20H; 1.5, m, 4H; 2, s, 3H; 4.2, m, 4H; 5.5, s, 1H; 6.2, s, 1H; 6.6; s, 1H.

Example 2

Preparation of N,N'-bis(2.4-dibenzylamino)-6-methylpyrimidine (PY8)

8.15 g of 2,4-dichloro-methyl-pyrimidine (50 mmol) are heated with 16 g of benzylamine (150 mmol) and 20.73 g of potassium carbonate (150 mmol) in 20 ml of dioxane for 16 hours at 100° C. After cooling, the product is taken up in 300 ml of ethyl acetate and washed with 0.5 mol/liter of sodium hydroxide solution and saturated sodium chloride solution. The product is concentrated in vacuo and then benzylamine is distilled off for 2 hours at from 105 to 120° C. under a rotary slide valve vacuum, and the product is recrystallised from isopropanol. N,N'-Bis(2,4-dibenzylamino)-6-methylpyrimidine is obtained in a yield of 76%. Purity: GC 100% NMR ($^1$H in DMSO, ppm): 2, s, 3H; 4.45, m, 4H; 5.6, s, 1H; 6.95, s, 1H; 7.25, m, 11H.

Example 3

Preparation of N,N'-bis(2.4-diphenylethylamino)-6-methylpyrimidine (PY9)

8.15 g of 2,4-dichloro-6-methyl-pyrimidine (50 mmol) are heated with 18.17 g of phenyl-ethylamine (150 mmol) and 20.73 g of potassium carbonate (150 mmol) in 20 ml of dioxane for 16 hours at 100° C. After cooling, the product is taken up in 300 ml of ethyl acetate and washed with 0.5 mol/liter of sodium hydroxide solution and saturated sodium chloride solution. The product is concentrated in vacuo and then phenylethylamine is distilled off for 2 hours at 150° C. under a rotary slide valve vacuum and the product is recrystallised from isopropanol. N,N'-Bis(2,4-diphenylethylamino)-6-methylpyrimidine is obtained in a yield of 98%.

Purity: GC 100% HPLC 98%

NMR ($^1$H in DMSO, ppm): 2, s, 3H; 2.9, t, 4H; 3.45, m, 4H; 5.6, s, 1H; 6.45, s, 1H; 6.8, s, 1H; 7.25, m, 10H.

Example 4

Preparation of 4-hydroxy-2-phenylamino-6-phenylpyrimidine 7 g (20 mmol) of phenylguanidine carbonate are reacted in 5 ml of absolute ethanol with 27.2 g (80 mmol) of a 20% sodium ethanolate solution. 11.5 g of ethylbenzoyl acetate (59.8 mmol) are added dropwise thereto in the course of 15 minutes at 75° C. The reaction mass is then stirred for 15 hours at 70° C. and, after cooling, is extracted with 50 ml of di-chloromethane and washed three times with 40 ml of water/3 ml of acetic acid.

The organic phase is dried over sodium sulfate and concentrated by evaporation.

5.86 g (55.7% of theory) of 4-hydroxy-2-phenylamino-6-phenylpyrimidine are obtained.

NMR ($^1$H in DMSO, ppm): 6.45, s, 1H; 7.05, t, 1H; 7.4, t, 2H; 7.5, m, 3H; 7.75, d, 2H; 8, m, 2H; 9, s, 11H; 11.05, s, 1H.

Example 5

Preparation of 4-chloro-2-phenylamino-6-phenylpyrimidine 2 g (7.6 mmol) are reacted in 10 ml of toluene with 3.5 g of phosphorus oxychloride. The reaction mass is heated to 80° C and 1.53 g of triethylamine (15.1 mmol) are added dropwise thereto in the course of 20 minutes. After a reaction time of 2 hours at 80° C., the mass is cooled in an ice bath and 28 ml of 4M sodium hydroxide solution are added dropwise thereto.

The aqueous phase is extracted three times with ethyl acetate.

After concentration of the organic phase by evaporation, 2.12 g (99.1% of theory) of 4-chloro-2-phenyl-amino-6-phenylpyrimidine are obtained.

NMR ($^1$H in DMSO, ppm): 7, t, 11H; 7.3, t, 2H; 7.55, m, 4H; 7.8, d, 2H; 8.2, m, 2H; 10.05, s, 11H.

Example 6

Reaction of 4-chloro-2-phenylamino-6-phenylpyrimidine with amines

The reactions are carried out in parallel robotically.

56.3 mg of 4-chloro-2-phenylamino-6-phenylpyrimidine (0.2 mmol) are dissolved in 0.5 ml of dioxane. 38.7 mg of diisopropylamine (0.3 mmol) and 3 mmol of amine are added thereto and the reaction mixture is heated at 85° C. for 21 hours. After cooling, the mass is extracted with 2 ml of dichloromethane and washed three times with 1.125 ml of acetic add (13% in water) and 1.2 ml of sodium hydroxide solution.

The organic phases are dried and lyophillsed.

The compounds (PY10)-(PY29) (see Table 1) are prepared according to this method. They were analysed by LC-MS.

30.74 g of compound C (87% of theory) are obtained.

Purity in HPLC: 99%

NMR (in $CD_2Cl_2$ in ppm): 0.9, t, 3H; 1.3, m, 10H; 1.6, qt, 2H; 2.2, s, 3H; 3.35, m, 2H; 5.6, s, 1H; 6.7, s, 1H.

Example 8

Preparation of the Compound of Formula D 18.96 g (0.08 mol) of the compound of formula C are reacted in 60 ml of toluene with 36.85 g of phosphorus oxychloride. The reaction mass is heated to 80° C. After a reaction time of 2 hours at 80° C., the mass is cooled in an Ice bath and 4M sodium hydroxide solution is added dropwise thereto. The aqueous phase is extracted three times with toluene.

After concentration of the organic phase by evaporation, 20.04 g (98% of theory) of the compound of formula D are obtained.

Purity in GC: 100%

NMR (in $CD_2Cl_2$ in ppm): 0.8, t, 3H; 1.3, m, 10H; 1.55, qt, 2H; 2.2, s, 3H; 3.3, q, 2H; 5.25, a, 1H; 6.35, s, 1H.

Example 9

Preparation of the Compound of Formula PY44

12.96 g of compound D (0.048 mol) are mixed with 6.19 g of di-isopropylamine (0.048 mol) in 60 ml of dioxane and

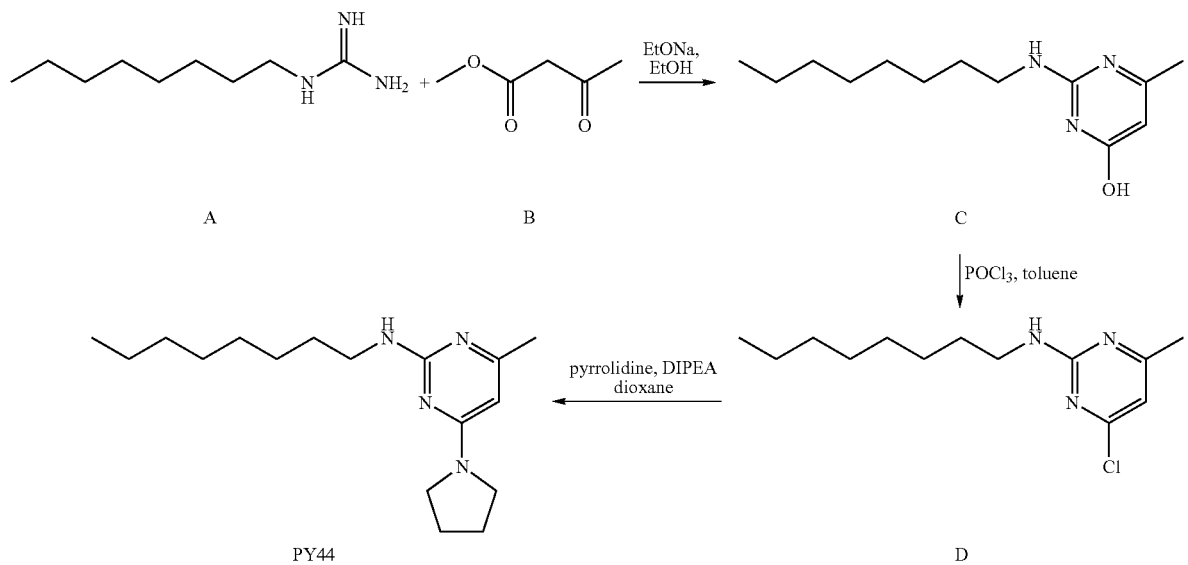

Example 7

Preparation of the Compound of Formula C 34.65 g of octylguanidine acetate A (0.15 mol) are reacted in 30 ml of ethanol with 102 g of 20% sodium ethanolate solution in ethanol (0.3 mol). The reaction mixture is heated to 75° C., and 26.15 g of methyl acetate B (0.22 mol) are added thereto in the course of one hour, and the mixture is stirred for 12 hours. After cooling, the reaction mass is diluted with dichloro-methane and washed three times with water/acetic add and twice with sodium hydroxide solution. The combined alkaline aqueous phases are adjusted to pH 6 with acetic acid and extracted with dichloromethane, dried over sodium sulfate and concentrated by evaporation.

heated at reflux. 4.9 g of pyrrolidine (0.057 mol) are added dropwise thereto in the course of 25 minutes and the reaction mixture is stirred at reflux for 29 hours. After cooling, the reaction mass is diluted with dichloromethane and washed three times with water/acetic acid and twice with sodium hydroxide solution. The organic phase is dried over sodium sulfate and concentrated by evaporation. 12.73 g of compound PY44 (91.4% of theory) are obtained.

Purity in GC: 100%

NMR ($CD_2Cl_2$ in ppm): 0.8, t, 3H; 1.2, m, 10H; 1.45, qt, 2H; 1.85, m, 4H; 2, s, 3H; 3.2-3.3, m (2 signals), 6H; 4.7, s, 1H; 5.45, s, 1H.

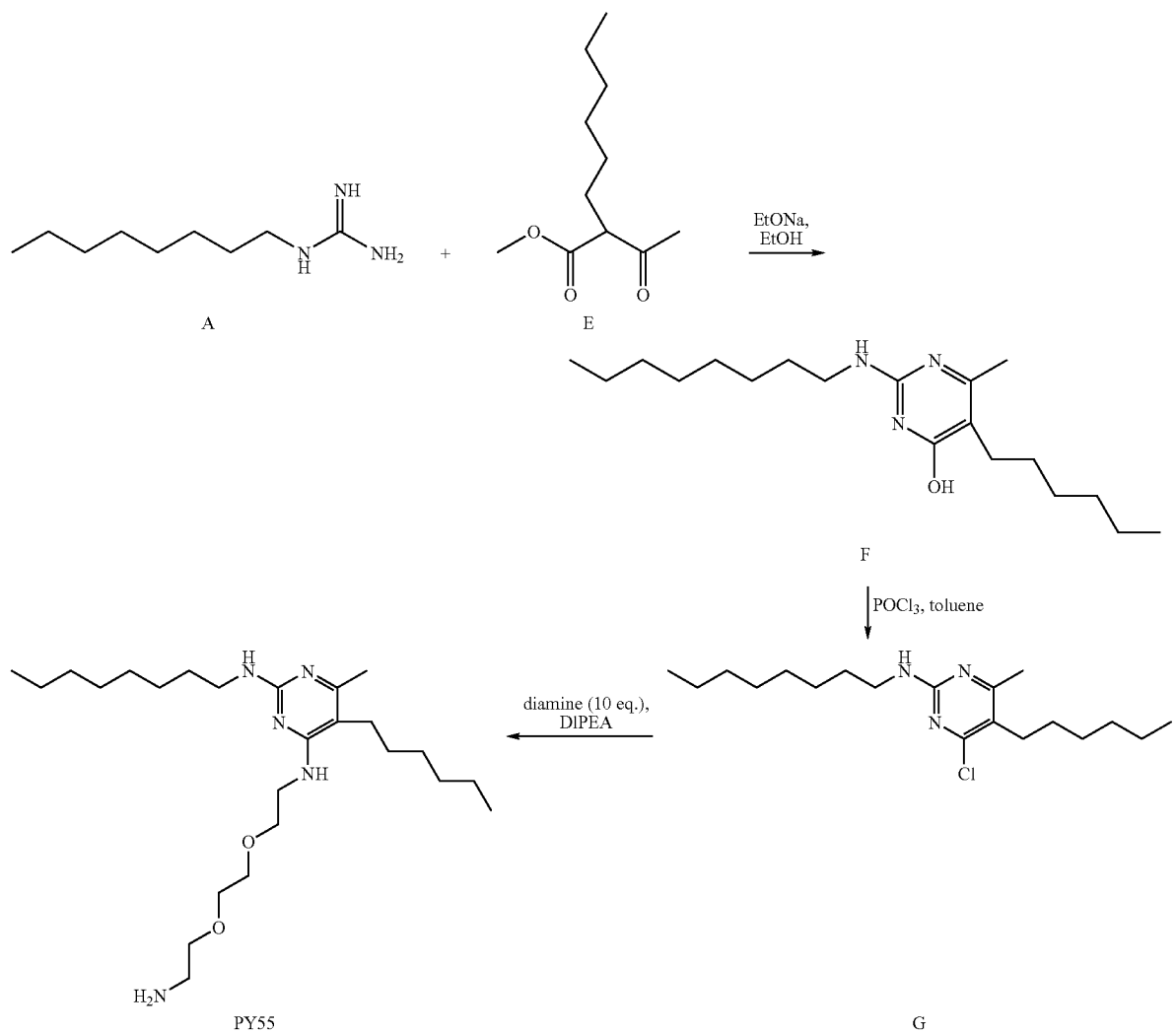

Example 10

Preparation of the Compound of Formula F 18.48 g of octylguanidine acetate A (0.08 mol) are reacted in 15 ml of ethanol with 54.4 g of 20% sodium ethanolate solution in ethanol (0.16 mol). The reaction mixture is then heated to 75° C and 24 g of methyl 2-hexylacetoacetate E (0.12 mol) are added thereto in the course of 30 minutes, and the mixture is stirred overnight. After cooling, the reaction mass is diluted with dichloromethane and washed twice with water/acetic acid. The organic phase is dried over sodium sulfate and concentrated by evaporation. The crude product is recrystallised from acetone. 14.86 g of compound F (57.9% of theory) are obtained.

LC-MS: a compound having M=321.

Example 11

Preparation of the Compound of Formula G 13.16 g (0.041 mol) of a compound of formula F are reacted in 40 ml of toluene with 18.89 g of phosphorus oxychloride. The reaction mass is heated to 80° C. After a reaction time of 2 hours at 80° C., the mass is cooled in an ice bath and 4M sodium hydroxide solution is added dropwise thereto. The aqueous phase is extracted three times with toluene.

After concentration of the organic phase by evaporation, 13.65 g (98% of theory) of the compound of formula G are obtained.

Purity in GC: 100%

NMR (CD$_2$Cl$_2$ in ppm): 0.9, m, 6H; 1.3, m, 18H; 1.5, m, 2H; 1.6, m, 2H; 2.4, s, 3H; 2.6, t, 2H; 3.4, q, 2H; 5.6, s, 1H.

Example 12

Preparation of the Compound of Formula PY55

11.88 g of compound G (0.035 mol) are stirred with 51.87 g of 1,8-diamino-3,6-dioxaoctane (0.35 mol) and 6.77 g of diisopropylamine (0.0525 mol) at 110° C. for 23 hours. After cooling, the reaction mass is diluted with dichloromethane and washed three times with water and twice with water/acetic acid. The combined aqueous phases are adjusted to pH 9 with sodium hydroxide solution and extracted with dichloromethane, dried over sodium sulfate and concentrated by evaporation. 14.45 g of compound PY55 (64.6% of theory) are obtained.

Purity in GC: 100%

NMR (CD$_2$Cl$_2$ in ppm): 0.9, m, 6H; 1.3, m, 20H; 1.55, m, 2H; 2.15, s, 3H; 2.3, t, 2H; 2.4, s, 2H; 2.8, t, 2H; 3.3, q, 2H; 3.45, t, 2H; 3.6, m, 8H; 5.1, s, 1H; 5.7, s, 1H.

Example 13

Determination of the Minimum Inhibiting Concentration (MIC value) in Microtiter Plates Nutrient Medium:
  Casein/soybean flour peptone bouillon for the preparation of the precultures of the test bacteria and yeast.

Examples of Test Organisms:
  Bacteria: *Staphylococcus aureus* ATCC 6583
    *Corynebacterium xerosis* ATCC 373 (a)
    *Actinomyces viscosus* ATTC 43146
    *Escherichia Coli* ATTC 10536

Procedure:
  The test substances are predissolved in dimethyl sulfoxide (DMSO) and tested in a serial dilution of 1:2.
  Bacteria and yeast are cultured overnight in CASO bouillon.
  All test organism suspensions are adjusted to an organism count of 1-5×10$^8$ CFU/ml with 0.85% sodium chloride solution.
  The test substances are prepipetted into microtiter plates in an amount of 8 µl per well.
  The previously adjusted organism suspensions are diluted 1:100 in CASO bouillon and added to the test substances in an amount of 192 µl per well.
  The test batches are incubated for 48 hours at 37° C.
  After incubation, the growth is determined by reference to the turbidity of the test batches (optical density) at 620 nm in a microplate reader.
  The minimum inhibiting concentration (MIC value) is the concentration of substance at which (compared with the growth control) an appreciable inhibition of the growth (≦20% growth) of the test organisms is ascertained.
  Three microtiter plates are used for each test organism and substance concentration.
  Table 2 shows the microbiological test results:

TABLE 2

Determination of the minimum inhibiting concentration in microtitre plates

| Compound of formula | MIC sa | MIC ec | MIC cx | MIC av |
|---|---|---|---|---|
| (PY1) | 11 | >120 | 6 | 6 |
| (PY2) | 105 | >120 | <3.75 | 26 |
| (PY3) | 43 | >120 | 11 | 11 |
| (PY4) | 79 | >120 | 20 | 20 |
| (PY5) | <3.75 | >120 | <3.75 | <3.75 |
| (PY6) | 51 | >120 | 13 | 51 |
| (PY7) | 32 | >120 | 4 | 8 |
| (PY8) | 17 | 34 | 8 | 8 |
| (PY9) | 5 | 37 | <3.75 | <3.75 |
| (PY10) | 8 | >120 | <3.75 | |
| (PY11) | 25 | >120 | <3.75 | |
| (PY12) | 32 | 64 | <3.75 | |
| (PY13) | 9 | >120 | <3.75 | |
| (PY14) | 58 | 116 | 29 | |
| (PY15) | 15 | >120 | 7 | |
| (PY16) | 37 | >120 | <3.75 | |

TABLE 2-continued

Determination of the minimum inhibiting concentration in microtitre plates

| Compound of formula | MIC sa | MIC ec | MIC cx | MIC av |
|---|---|---|---|---|
| (PY17) | 4 | >120 | <3.75 | |
| (PY18) | <3.75 | >120 | <3.75 | |
| (PY19) | 32 | 8 | 8 | |
| (PY20) | 29 | 29 | 15 | |
| (PY21) | <3.75 | >120 | <3.75 | |
| (PY22) | 40 | >120 | 20 | |
| (PY23) | 160 | >120 | 40 | |
| (PY24) | >120 | >120 | 16 | |
| (PY25) | 76 | >120 | 10 | |
| (PY26) | >120 | >120 | 15 | |
| (PY27) | >120 | >120 | 60 | |
| (PY28) | 40 | 160 | 10 | |
| (PY29) | 10 | >120 | <3.75 | |
| PY30 | 16.5 | >120 | 16.5 | 8.25 |
| PY31 | <3.75 | >120 | <3.75 | <3.75 |
| PY32 | 19.5 | >120 | <3.75 | <3.75 |
| PY33 | <3.75 | 9.75 | <3.75 | <3.75 |
| PY34 | 8 | >120 | <3.75 | <3.75 |
| PY35 | 17 | 34 | 8.5 | 8.5 |
| PY36 | <3.75 | >120 | <3.75 | <3.75 |
| PY37 | <3.75 | >120 | <3.75 | <3.75 |
| PY38 | 33 | 66 | 8.25 | 8.25 |
| PY39 | <3.75 | >120 | <3.75 | <3.75 |
| PY40 | 9 | >120 | <3.75 | <3.75 |
| PY41 | 64 | >120 | 64 | 64 |
| PY42 | <3.75 | >120 | <3.75 | <3.75 |
| PY43 | 27 | 54 | 13.5 | 6.75 |
| PY44 | <3.75 | 30 | <3.75 | <3.75 |
| PY45 | <3.75 | 58 | <3.75 | <3.75 |
| PY46 | 7.25 | >120 | <3.75 | <3.75 |
| PY47 | <3.75 | 35 | <3.75 | <3.75 |
| PY48 | 32 | 128 | 8 | 8 |
| PY49 | 64 | >120 | 32 | 16 |
| PY50 | 64 | 64 | 32 | 16 |
| PY51 | >120 | >120 | <3.75 | <3.75 |
| PY52 | 9.25 | 9.25 | <3.75 | <3.75 |
| PY53 | 108 | >120 | <3.75 | <3.75 |
| PY54 | <3.75 | 36 | <3.75 | <3.75 |
| PY55 | <3.75 | <3.75 | <3.75 | <3.75 |
| PY56 | 18.5 | 9.25 | <3.75 | <3.75 |
| PY57 | 9.5 | >120 | <3.75 | <3.75 |
| PY58 | 17 | >120 | <3.75 | <3.75 |
| PY59 | 19.5 | >120 | 9.75 | 9.75 |
| PY60 | 27 | >120 | 13.5 | 6.75 |
| PY61 | 18.5 | >120 | 9.25 | 9.25 |
| PY62 | 76 | >120 | 19 | 9.5 |
| PY63 | 8.75 | >120 | <3.75 | <3.75 |
| PY64 | 36 | >120 | <3.75 | <3.75 |
| PY65 | <3.75 | <3.75 | <3.75 | <3.75 |
| PY66 | 18.5 | >120 | <3.75 | 7 |
| PY67 | <3.75 | >120 | <3.75 | <3.75 |
| PY68 | 6.25 | >120 | <3.75 | <3.75 |
| PY69 | <3.75 | >120 | <3.75 | <3.75 |
| PY70 | 31 | >120 | <3.75 | <3.75 |
| PY71 | 9 | >120 | <3.75 | <3.75 |
| PY72 | 31 | 15.5 | <3.75 | <3.75 |
| PY73 | 18 | 18 | <3.75 | <3.75 |
| PY74 | 34 | >120 | 8.5 | 8.5 |

Example 14

Determination of the Minimum Inhibiting Concentration MIC [ppm] of a Broadened Organism Spectrum Medium: Casein/soybean flour peptone agar (Merck)
  *Sabouraud 4% glucose agar (Merck)
Dilution medium: sterile 0.85% NaCl solution
Test organisms: *Staphylococcus aureus* ATCC 6853 and 9144
  *Staphylococcus epidermidis* ATCC 12228

C. xerosis ATCC 373 **
C. minutissimum ATCC 23348
Proplonibacterium acnes ATCC 6919
Escherichia coli ATCC 10536 and NCTC 8196
Proteus vulgaris ATCC 6896
Klebsiella pneumoniae ATCC 4352
Salmonella choleraesuis ATCC 9184
Pseudomonas aeruginosa ATCC 15442
*Candida albicans ATCC 10231
*Aspergillus niger ATCC 6275
Incubation: 24 hours at 37° C.
*3 days at 28° C.
Test solution: 1% stock solutions of all the test substances in a suitable solvent are prepared and diluted in serial dilutions (1:10, 1:100 and 1:1000 dilution), where possible diluted to such an extent that the end concentrations in agar are from 500 ppm to 10 ppm.

Test principle:
0.3 ml of the dilution stage in question is mixed with 15 ml of still-liquid nutrient medium.
When the nutrient substrate has solidified, 10 μl portions of a suitable organism dilution of the test strains in 0.85% NaCl solution are spotted onto the agar medium:

TABLE 3

Determination of the minimum inhibiting concentration MIC [ppm] of a broadened organism spectrum

| Microorganism | Compound of formula | | |
|---|---|---|---|
| | (PY5) | (PY8) | (PY9) |
| Staphylococcus aureus ATCC 6538 | 3.91 | 31.25 | 7.8 |
| Staphylococcus aureus ATCC 9144 | 3.91 | 31.25 | 7.8 |
| Staphylococcus epidermidis ATCC 12228 | 3.91 | 31.25 | 7.8 |
| C. xerosis ATCC 373** | 7.81 | 7.8 | 1.95 |
| C. minutissimum ATCC 23348 | 3.91 | 15.63 | 3.9 |
| Propionibacterium acnes ATCC 6919*** | 3.91 | 31.25 | 7.8 |
| Escherichia coli NCTC 8196 | >1000 | 31.25 | 15.63 |
| Escherichia coli ATCC 10536 | >1000 | 62.5 | 250 |
| Proteus vulgaris ATCC 6896 | >1000 | >500 | >500 |
| Klebsiella pneumoniae ATCC 4352 | 250 | 15.63 | 7.8 |
| Salmonella choleraesuis ATCC 9184 | >1000 | 62.5 | 250 |
| Pseudomonas aeruginosa ATCC 15442 | >1000 | >500 | >500 |
| Candida albicans ATCC 10231 | >1000 | 250 | 62.5 |
| Aspergillus niger ATCC 6275 | >1000 | 250 | 250 |

TABLE 3a

Determination of the minimum inhibiting concentration MIC°[ppm] of a broadened organism spectrum

| Microorganisms | (PY44) | (PY55) |
|---|---|---|
| Staphylococcus aureus ATCC 6538 | 7.8 | 7.8 |
| Staphylococcus aureus ATCC 9144 | 7.8 | 3.9 |
| Staphylococcus epidermidis ATCC 12228 | 3.9 | 7.8 |
| C. xerosis ATCC 373** | 3.9 | 3.9 |
| C. minutissimum ATCC 23348** | 3.9 | 3.9 |
| Propionibacterium acnes ATCC 6919*** | 3.9 | 3.9 |
| Escherichia coli NCTC 8196 | 15.63 | 7.8 |
| Escherichia coli ATCC 10536 | 62.5 | 7.8* |
| Proteus vulgaris ATCC 6896 | >500 | >500 |
| Klebsiella pneumoniae ATCC 4352 | 7.8 | 15.63 |
| Salmonella choleraesuis ATCC 9184 | 62.5 | 7.8 |
| Pseudomonas aeruginosa ATCC 15442 | >500 | >500 |
| Candida albicans ATCC 10231 | 250 | 125 |
| Aspergillus niger ATCC 6275 | 500 | 500 |

*very slow growth, no growth in the next dilution stage
**3 days incubation,
***3 days incubation under anaerobic conditions Example 15

Determination of the Minimum Inhibiting Concentration MIC (ppm) of a Broadened Organism Spectrum: Oral Organisms Medium: thioglycolate bouillon with hemin and menadione Columbia bouillon with hemin and menadione for P. gingivalis and P. nigrescens
Dilution medium: the appropriate amount of the substances was pipetted directly into the medium.
Test organisms: Actinobacillus actinomycetemcomitans ATCC 43718
Streptococcus gordonil ATCC 10558
Streptococcus mutans ATCC 33402
Actinomyces viscosus ATCC 43146
Fusobacterium nucleatum subsp. polymorphum ATCC 10953
Porphyromonas gingivalis ATCC 33277
Prevotella nigrescens ATCC 33563
Incubation: 7-10 days at 37° C anaerobic, or 24 hours aerobic with 10% $CO_2$ for Streptococci and A. actinomycetemcomitans
Test solution: Stock solutions of all the test substances in ethanol at 1500 ppm (w/w) are used.

Test Principle:
Bacteria are removed from blood agar plates using cotton wool buds and a suitable optical density (McFarland 0.5) is adjusted in an appropriate medium; that solution is used undiluted for F. nucleatum and P. nigrescens, and in a dilution of 1:20 for the other strains. 0.1 ml of bacterial culture is added per 2 ml of active ingredient solution and incubation is carried out as described above.

TABLE 4

Determination of the minimum inhibiting concentration MIC [ppm] of a broadened organism spectrum: oral organisms

| Microorganism | Compound of formula | | |
|---|---|---|---|
| | (PY5) | (PY8) | (PY9) |
| A. actinomycetemcomitans ATCC43718 | >15 | >15 | >15 |
| S. gordonii ATCC 10558 | 15 | >15 | 15 |
| S. mutans ATCC 33402 | 3.75 | >15 | 15 |
| A. viscosus ATCC 43146 | 3.75 | 3.75 | 3.75 |
| F. nucleatum subsp. Polymorphum ATCC 10953 | >15 | 15 | 15 |
| P. gingivalis ATCC 3277 | 7.5 | 15 | 7.5 |
| P. nigrescens ATCC 33563 | 15 | 15 | 7.5 |

| Microorganism | (PY44) | (PY55) |
|---|---|---|
| A. actinomycetemcomitans ATCC 43718 | >15 | 15 |
| S. gordonii ATCC 10558 | 7.5 | 3.8 |
| S. mutans ATCC 33402 | 7.5 | 7.5 |
| A. viscosus ATCC 43146 | 3.8 | 3.8 |
| F. nucleatum subsp. polymorphum ATCC 10953 | 3.8 | 7.5 |
| P. gingivalis ATCC 3277 | 3.8 | 3.8 |
| P. nigrescens ATCC 33563 | 3.8 | 3.8 |

What is claimed is:
1. A method for the antimicrobial treatment of a surface of a plastic, which method comprises contacting said surface of a plastic with a surface coating composition containing an antimicrobially effective amount of a 2,4-bis(alkylamino)pyrimidine of formula

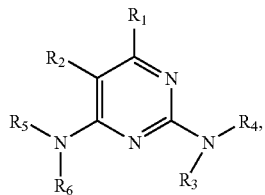

wherein
- $R_1$ is methyl,
- $R_2$ is hydrogen,
- $R_3$ is hydrogen,
- $R_4$ is butyl, amyl, hexyl, heptyl, octyl, nonyl, decyl, undecyl or dodecyl and
- $R_5$ and $R_6$ together form a pyrrolidine, piperidine or morpholine ring;

or
- $R_1$ is methyl,
- $R_2$ is hydrogen,
- $R_3$ and $R_4$ together form a pyrrolidine, piperidine or morpholine ring,
- $R_5$ is hydrogen and
- $R_6$ is butyl, amyl, hexyl, heptyl, octyl, nonyl, decyl, undecyl or dodecyl;

or
- $R_1$ is methyl,
- $R_2$ is straight chain $C_3$-$C_8$alkyl,
- $R_3$ and $R_5$ are hydrogen,
- $R_4$ is butyl, amyl, hexyl, heptyl, octyl, nonyl, decyl, undecyl or dodecyl and
- $R_6$ is di-$C_1$-$C_6$alkylamino-$C_1$-$C_6$alkyl, mono-$C_1$-$C_6$alkylamino-$C_1$-$C_6$alkyl, or —$(CH_2)_2$—(O—$(CH_2)_2)_{1-2}$—$NH_2$.

2. A method according to claim 1 wherein
- $R_1$ is methyl,
- $R_2$ is hydrogen,
- $R_3$ is hydrogen,
- $R_4$ is butyl, amyl, hexyl, heptyl, octyl, nonyl, decyl, undecyl or dodecyl and
- $R_5$ and $R_6$ together form a pyrrolidine, piperidine or morpholine ring;

or
- $R_1$ is methyl,
- $R_2$ is hydrogen,
- $R_3$ and $R_4$ together form a pyrrolidine, piperidine or morpholine ring,
- $R_5$ is hydrogen and
- $R_6$ is butyl, amyl, hexyl, heptyl, octyl, nonyl, decyl, undecyl or dodecyl.

3. A method according to claim 2 wherein
- $R_1$ is methyl,
- $R_2$ is hydrogen,
- $R_3$ is hydrogen,
- $R_4$ is butyl, amyl, hexyl, heptyl, octyl, nonyl, decyl, undecyl or dodecyl and
- $R_5$ and $R_6$ together form a pyrrolidine;

or
- $R_1$ is methyl,
- $R_2$ is hydrogen,
- $R_3$ and $R_4$ together form a pyrrolidine,
- $R_5$ is hydrogen and
- $R_6$ is butyl, amyl, hexyl, heptyl, octyl, nonyl, decyl, undecyl or dodecyl.

4. A method according to claim 2 wherein
- $R_1$ is methyl,
- $R_2$ is hydrogen,
- $R_3$ is hydrogen,
- $R_4$ is hexyl, heptyl, octyl, nonyl or decyl and
- $R_5$ and $R_6$ together form a pyrrolidine, piperidine or morpholine ring;

or
- $R_1$ is methyl,
- $R_2$ is hydrogen,
- $R_3$ and $R_4$ together form a pyrrolidine, piperidine or morpholine ring,
- $R_5$ is hydrogen and
- $R_6$ is hexyl, heptyl, octyl, nonyl or decyl.

5. A method according to claim 4 wherein
- $R_1$ is methyl,
- $R_2$ is hydrogen,
- $R_3$ is hydrogen,
- $R_4$ is hexyl, heptyl, octyl, nonyl or decyl and
- $R_5$ and $R_6$ together form a pyrrolidine ring;

or
- $R_1$ is methyl,
- $R_2$ is hydrogen,
- $R_3$ and $R_4$ together form a pyrrolidine,
- $R_5$ is hydrogen and
- $R_6$ is hexyl, heptyl, octyl, nonyl or decyl.

6. A method according to claim 5 wherein
- $R_1$ is methyl,
- $R_2$ is hydrogen,
- $R_3$ is hydrogen,
- $R_4$ is octyl and
- $R_5$ and $R_6$ together form a pyrrolidine ring;

or
- $R_1$ is methyl,
- $R_2$ is hydrogen,
- $R_3$ and $R_4$ together form a pyrrolidine,
- $R_5$ is hydrogen and
- $R_6$ is octyl.

7. A method according to claim 1 wherein
- $R_1$ is methyl,
- $R_2$ straight chain $C_3$-$C_8$alkyl,
- $R_3$ and $R_5$ are hydrogen,
- $R_4$ is butyl, amyl, hexyl, heptyl, octyl, nonyl, decyl, undecyl or dodecyl
- $R_6$ is di-$C_1$-$C_6$alkylamino-$C_1$-$C_6$alkyl, mono-$C_1$-$C_6$alkylamino-$C_1$-$C_6$alkyl, or —$(CH_2)_2$—(O—$(C_2)_2)_{1-2}$—$NH_2$.

8. A method according to claim 7 wherein
$R_6$ is —$(C_2)_2$—(O—$(CH_2)_2)_{1-2}$—$NH_2$.

9. A method according to claim 7 wherein
$R_4$ is hexyl, heptyl, octyl, nonyl, decyl.

10. A method according to claim 8 wherein
$R_4$ is hexyl, heptyl, octyl, nonyl, decyl.

11. A method according to claim 8 wherein $R_2$ is hexyl and $R_4$ is octyl.

* * * * *